US00PP09800P

United States Patent [19]

Zaiger et al.

[11] Patent Number: Plant 9,800

[45] Date of Patent: Feb. 11, 1997

[54] PEACH TREE 'SIESTA GEM'

[76] Inventors: Chris F. Zaiger, 929 Grimes Ave.; Leith M. Gardner, 1207 Grimes Ave.; Gary N. Zaiger, 1907 Elm Ave.; Grant G. Zaiger, 4005 California Ave., all of Modesto, Calif. 95358

[21] Appl. No.: 577,769

[22] Filed: Dec. 22, 1995

[51] Int. Cl.[6] ..... A01H 5/00

[52] U.S. Cl. ..... Plt./43.1

[58] Field of Search ..... Plt./43.1

*Primary Examiner*—James R. Feyrer

[57] ABSTRACT

The new and distinct variety of peach tree has the following unique combination of desirable features:

1. Early maturity of large size fruit.
2. Fruit with an attractive red blush skin.
3. Fruit with good flavor and eating quality.
4. Producing firm fruit with good storage and shipping quality.
5. Heavy and regular production of fruit.
6. Relatively uniform size of fruit throughout the tree.
7. Vigorous, upright growth.

1 Drawing Sheet

ORIGIN OF THE VARIETY

The new and distinct variety of peach tree was originated by us in our experimental orchard located near Modesto, Calif., as a first generation cross between two selected seedlings, field identification numbers 34GA1155 and 36EB346. The maternal parent (field identification number 34GA1155) originated from a seedling selection from an open pollinated May Grand Nectarine (U.S. Pat. No. P.P. 2,794) crossed with a peach of unknown parentage. This selection was then crossed with an open pollinated seedling of Sam Houston Peach (non-paented). The paternal parent (field identification number 36EB346) originated from a first generation cross of Tasty Gold Nectarine (U.S. Pat. No. P.P. 5,623) crossed with May Crest Peach (U.S. Pat. No. P.P. 4,064).

ASEXUAL REPRODUCTION OF THE VARIETY

The present new and distinct variety of peach tree was asexually propagated by budding, as performed by us in our experimental orchard located near Modesto, Calif. which shows that all characteristics of the tree and its fruit are established and transmitted through succeeding asexual propagation and run true to the original tree in all respects.

SUMMARY OF THE VARIETY

The herein described new variety of peach tree is of large size; vigorous, upright growth; a productive and regular bearer of large, firm, yellow flesh, clingstone fruit with good flavor and eating quality. The frit is further characterized by having relativey uniform, large size throughout the tree; having good storage and shipping quality, having an attractive red blush skin, and ripening in the early maturity season. In comparison to the early maturing May Crest Peach (U.S. Pat. No. P.P. 4,064), the new variety has greater production of larger fruit and is approximately 7 to 8 day later in maturity.

DESCRIPTION OF THE PHOTOGRAPH

The accompanying photographic illustration shows typical specimens of the foliage and frit of our present new variety of peach tree. The illustration is of the upper and lower surface of the leaves; the exterior and sectional view of the fruit divided in the suture plane to reveal flesh color; the pit cavity and a stone remaining in place. The photographic illustration was taken shortly after the fruit was picked at maturity (firm ripe) and the colors are as nearly true as is reasonably possible in a color representation of this types.

DESCRIPTION OF THE VARIETY

The following is a detail botanical description of the present new variety of peach tree, its flowers, foliage and fruit, as based on observations of specimens growth near Modesto, Calif. with color terminology (except those in common terms) in accordance with Reinhold Color Atlas by A. Kornerup and J. H. Wanscher.

Tree:
- *Size.*—Large.
- *Vigor.*—Vigorous.
- *Growth.*—Upright.
- *Density.*—Medium dense.
- *Productivity.*—Productive.
- *Bearer.*—Regular.

Trunk:
- *Size.*—Large.
- *Texture.*—Medium shaggy.
- *Color.*—Soot brown to coffee brown (5-F-5) to (5-F-7).

Branches:
- *Size.*—Medium.
- *Texture.*—Smooth to medium rough—varies with age of growth.
- *Lenticels.*—Numerous. Large size.
- *Color.*—Light brown to dull brown (5-D-5) to (5-E-6) varies with age of growth.

Leaves:
- *Size.*—Large. Average length — 6". Average width — 1⅝".
- *Form.*—Lanceolate.
- *Texture.*—Smooth.
- *Margin.*—Crenate.
- *Thickness.*—Medium.
- *Petiole.*—Medium length. Medium thickness.
- *Glands.*—Reniform. Number varies from 1 to 4. Average number 2. Positioned on upper portion of petiole and base of leaf blade.
- *Color.*—Upper surface — green to deep green (28-F-6) to (28F-8). Lower surface — grayish green to dull green (28-E-6) to (28-E-8).

Flower buds:
*Size.*—Large.
*Length.*—Medium.
*Form.*—Plump.
Flower:
*Size.*—Large-showy.
*Blooming period.*—Mar. 6, 1994 to Mar. 11, 1994. Varies slightly with climatic conditions.
*Pollen.*—Present.
*Color.*—Pink.
Fruit:
*Maturity when described.*—Firm ripe.
*Date of first picking.*—May 26, 1994.
*Date of last picking.*—Jun. 1, 1994.
*Size.*—Large. Average diameter axially 3". Average transversely in suture plane 2⅞".
*Form.*—Nearly Globose — slightly elongated in suture plane.
*Suture.*—Shallow, nearly rounded, extends from base to apex.
*Cavity.*—Rounded to slightly elongated in suture plane.
*Base.*—Retuse.
*Apex.*—Varies from rounded to slightly retuse.
Flesh:
*Ripens.*—Relatively uniform, only slightly earlier at apex.
*Texture.*—Firm.
*Fibers.*—Few, small, tender.
*Juice.*—Moderate.
*Flavor.*—Good, mild, good balance between sugar and acid.
*Eating quality.*—Good.
*Color.*—Light yellow to yellow (4-A-4) to (4-A-5). Pit cavity dull yellow to grayish yellow (3-B-4) to (3-B-5). Slight bleeding of pinkish red from pit cavity toward apex, varies with fruit maturity.
Skin:
*Thickness.*—Medium.
*Texture.*—Medium, tenacious to flesh.
*Tendency to crack.*—None.
*Down.*—Moderate, medium length.
*Color.*—Light yellow to pale orange ground color (4-A-5) to (5-A-5). Approximately 50% overspread with light red blush (9-A-7) to (9-B-7).
Stone:
*Type.*—Clingstone.
*Size.*—Large. Average length 1½". Average breadth 1⅛". Average thickness ⅝.
*Form.*—Oval to ovoid.
*Base.*—Usually straight, varies from straight to round.
*Apex.*—Cuspidate.
*Side.*—Equal to unequal.
*Surface.*—Furrowed toward apex, pitted throughout, heavier toward base, pits vary from round to elongated.
*Tendency to split.*—Very slight.
*Color.*—Tan to light brown (7-C-4) to (7-D-5).
Use: Dessert.
*Market.*—Local and long distance.
Keeping quality: Good.
Shipping quality: Good.

The new variety of peach tree, its flowers, foliage and fruit herein described may vary in slight detail due to climate, soil conditions and cultural practices under which the variety may be grown; the present description being of the variety grown under the ecological conditions prevailing near Modesto, Calif.

We claim:

1. A new and distinct variety of peach tree, substantially as illustrated and described, characterized by its large size, vigorous, upright growth, and being a productive and regular bearer of large, yellow flesh, clingstone fruit with good flavor and eating quality; the fruit is further characterized by being nearly globose in shape, having firm flesh with good storage and shipping abiliy, having an attractive red blush skin, and in comparison to the variety May Crest Peach (U.S. Pat. No. P.P. 4,064) the new variety has heavier production of larger size fruit.

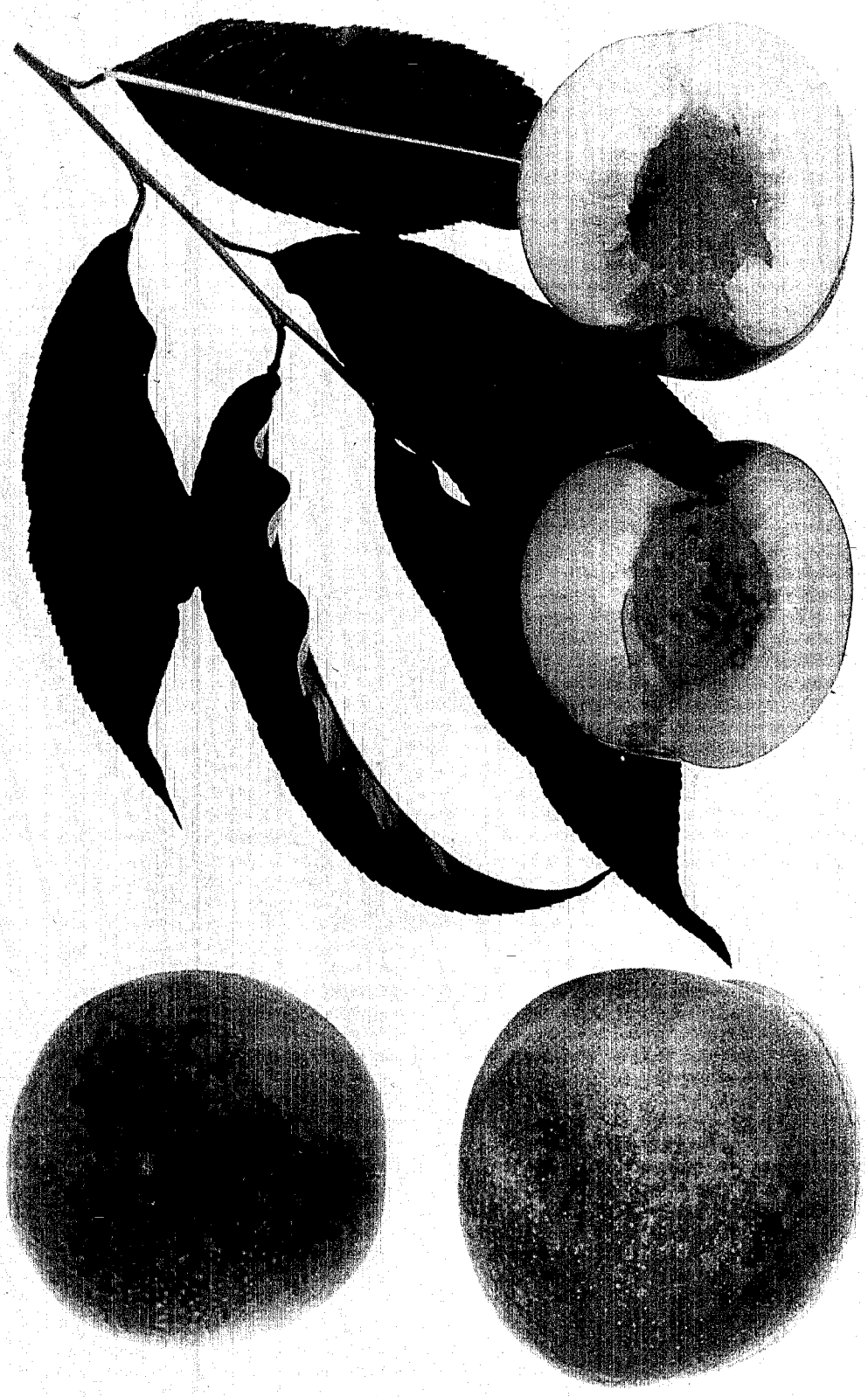

* * * * *